United States Patent [19]

Doan et al.

[11] Patent Number: 5,158,547
[45] Date of Patent: Oct. 27, 1992

[54] DRUG ADMINISTRATION DEVICE OVER FULL PROTECTION VALVE

[75] Inventors: Phong Doan, Newhall, Calif.; William S. Nettecoven, Stillwater, Minn.

[73] Assignee: Medtronic, Inc., Minneapolis, Minn.

[21] Appl. No.: 681,955

[22] Filed: Apr. 8, 1991

[51] Int. Cl.⁵ .............................. A61M 11/00
[52] U.S. Cl. ........................ 604/93; 604/132; 604/247; 604/256
[58] Field of Search ........ 604/247, 174, 175, 180, 604/244, 131, 93, 97, 98, 99, 256, 132, 133, 141, 143

[56] References Cited

U.S. PATENT DOCUMENTS

| | | |
|---|---|---|
| 4,193,397 | 3/1980 | Tucker et al. ............. 604/175 X |
| 4,772,263 | 9/1988 | Dorman et al. ............ 604/132 |
| 4,832,054 | 5/1989 | Bark .......................... 604/93 X |
| 4,846,806 | 7/1989 | Wigness et al. ........... 604/175 |
| 4,902,278 | 2/1990 | Maget et al. .............. 604/132 |
| 4,968,301 | 11/1990 | di Palma et al. .......... 604/132 |
| 4,978,338 | 12/1990 | Melsky et al. ............ 604/132 |

Primary Examiner—John D. Yasko
Attorney, Agent, or Firm—Harold R. Patton; Terry L. Wiles; John L. Rooney

[57] ABSTRACT

A technique for protecting an implantable drug administration device from damage caused by over filling. The protection is implemented using an automatic valve positioned between the puncturable sealing septum and the reservoir. This automatic valve is operated volumetrically by coupling the valve actuator to the diaphragm which separates the drug chamber from the fluid volume compensation chamber. When the diaphragm flexes to the maximum fill position, the valve actuator closes the automatic valve, thus prohibiting any further transfer to the reservoir.

10 Claims, 8 Drawing Sheets

DRUG ADMINISTRATION DEVICE OVER FULL PROTECTION VALVE

BACKGROUND OF THE INVENTION

1. Field of the Invention

The present invention generally relates to implantable medical devices, and more particularly, relates to implantable medical devices for the administration of a drug.

2. Description of the Prior Art

It has been known for some time to implant drug administration devices. Such devices employ a reservoir which is filled by the attending medical personnel. The drug material, usually a liquid, is dispensed within the body of a patient over time. This dispensing may be accomplished at a constant rate associated with the pressure under which the liquid drug is held within the reservoir. Alternatively, the dispensing may be at a programmed rate using a microprocessor driven pump.

A common problem associated with the various designs of implantable drug administration devices is that associated with over filling. In normal operation, the reservoir is filled percutaneously from a hypodermic syringe. The medical person filling the reservoir has historically needed to rely upon tactile pressure to determine the state of fill of the reservoir. This problem is made all the more difficult as the various designs have used fluids to back-fill the volume of the reservoir in an attempt to maintain a constant pressure within the reservoir, independent of remaining drug volume.

The result is that the filling process occurs at an almost constant pressure until the reservoir is completely filled. Any additional liquid injected may cause severe damage to the drug administration device, and leakage to the medical detriment of the patient. The difficulty with prior art drug administration devices is the lack of a precise and reliable over fill protection device to prevent damage to the drug administration device and uncontrolled leakage.

SUMMARY OF THE INVENTION

The present invention overcomes the disadvantages of the prior art by providing a highly reliable means for protecting an implantable drug administration device from damage due to over filling. The over-fill protection is accomplished by fixedly attaching a valve actuator to the diaphragm, which separates the reservoir drug chamber from the chamber containing the fluorocarbon used for volume compensation.

The significance of this approach is that it is essentially operated by volumetric measurement. The valve is closed as a result of the drug reservoir expansion to the maximum allowable volume as determined by the amount of travel of the diaphragm at the point of attachment of the valve actuator. When maximum volume has been achieved, the valve actuator positively closes the filling valve, thus preventing any further injection of the liquid drug.

The filling valve is located in the channel between the drug reservoir and the puncturable septum. Therefore, any liquid drug which leaves the hypodermic syringe after the filling valve has been closed is trapped between the septum and the reservoir, thus protecting the patient.

Even though the automatic valve system has all of the simplicity associated with a completely mechanical system, it has but one moving part, the spring loaded valve actuator. The valve seats are fixed to the fill tube channel. Compressible closure elements, properly located on the valve actuator, sealingly engage the valve seats to close the valve. In this way, the automatic valve system operates in a highly reliable fashion, and is precisely actuated based upon reservoir volume.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein.

DETAILED DESCRIPTION OF THE PREFERRED EMBODIMENTS

Figure 1:
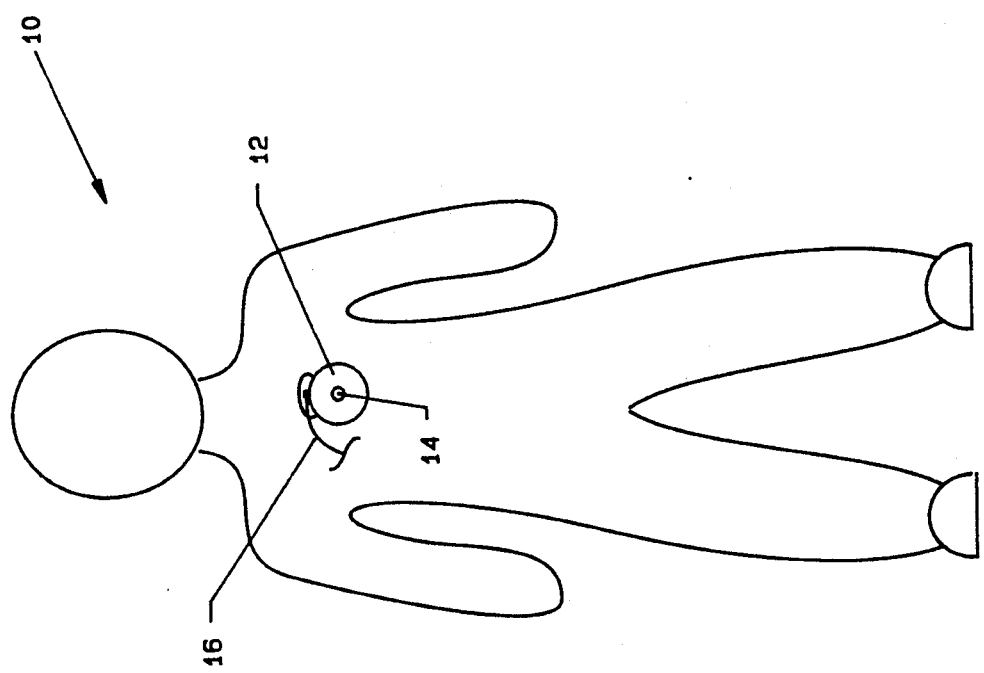
FIG. 1 is a schematic view of an implantable drug administration device employing the present invention as located within a patient.

FIG. 1 is a schematic diagram of patient 10 showing the location of implantable drug administration device 12. Attending medical personnel fill the reservoir of implantable drug administration device 12 percutaneously through fill port 14. The liquid drug is dispensed within the body of patient 10 through catheter 16 (only partially shown).

Implantable drug administration device 12 is preferably a programmable device such as the Model 8610 Drug Administration System of Medtronic, Inc. of Minneapolis, Minn. It is useful for dispensing precisely measured amounts of a liquid drug to a patient over time. This type of drug administration overcomes problems associated with patient compliance, topical rather than systemic delivery, and other known medical difficulties.

Figure 2:
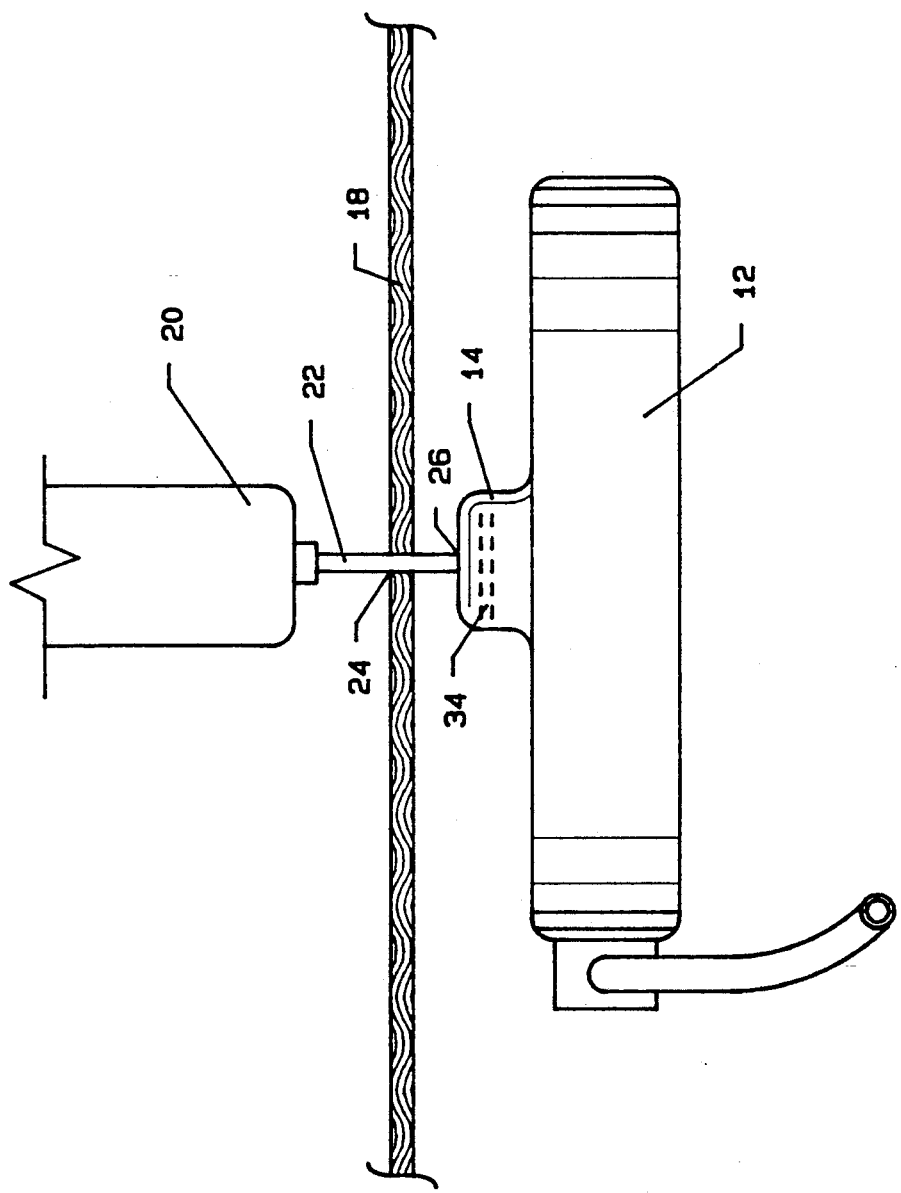
FIG. 2 is a side view of the drug administration device during filling.

FIG. 2 is a side view of implantable drug administration device 12 as implanted under skin layer 18 of patient 10. Fill port 14 is a small cylindrical protrusion located within the center of implantable drug administration device 12 and is directed toward skin layer 18. In this way, the process of filling the reservoir of implantable drug administration device 12 begins with tactilely locating fill port 14 by manual palpation.

Once fill port 14 has been located, needle 22 of hypodermic syringe 20 punctures skin layer 18 at point 24, and septum 34 of implantable drug administration device 12 at point 26. As implantable drug administration device 12 and fill port 14 have outer surfaces of a hard, biocompatible metal, such as titanium, needle 22 is directed toward point 26 of septum 34.

After septum 34 is punctured at point 26, the liquid drug is injected into the reservoir of implantable drug administration device 12 by distal advancement of the syringe plunger (not shown). Even though a precise amount of liquid drug can be dispensed in this fashion, in actual operation, after implantable drug administration device 12 has been in use for some time, it becomes difficult to ascertain the exact volume of liquid drug within the reservoir. For that reason, it is advantageous to employ the valve of the present invention to protect implantable drug administration device 12 from damage caused by over filling.

Figure 3:
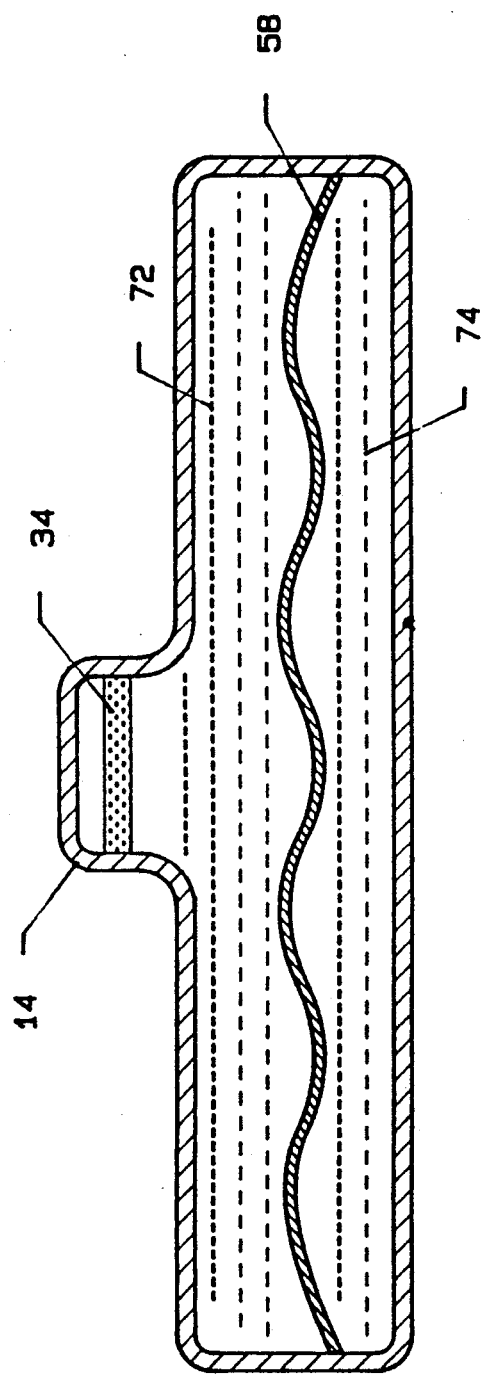
FIG. 3 is a cut away partial view of the key elements of the reservoir of the drug administration device.

FIG. 3 is a partially sectioned side view of implantable drug administration device 12 showing operation of the reservoir portion which is separated into two chambers by diaphragm 58. Preferably, diaphragm 58 is fabricated from a thin sheet of titanium or other inert metal. The lower chamber is back filled with a fluid 74 which serves to compensate for relative volumetric fluctuations in the two chambers. This compensation is readily accomplished by partial or total phase change of fluid 74. This results in a relatively constant pressure within the upper chamber, nearly independent of upper chamber volume.

The upper chamber contains liquid drug 72. As the upper chamber is filled, the noncompressible liquid drug 72 occupies a larger volume, forcing diaphragm 58 to decrease the volume of the lower chamber. Fluid 74 compensates by increasingly changing phase into a liquid, thus occupying a lesser volume. Similarly, as liquid drug 72 is dispensed to patient 10, the volume requirement in the upper chamber is decreased and compensation occurs as larger portions of fluid 74 are converted to a gas.

As can be seen, fill port 14 is preferably molded or stamped continuously from the same material as implantable drug administration device 12. It is invaginated to produce a central lumen in fluid communication with the upper chamber of the reservoir. The central lumen is sealed with septum 34 which is of a medical grade rubber or other puncturable, resealing material.

Figure 4:
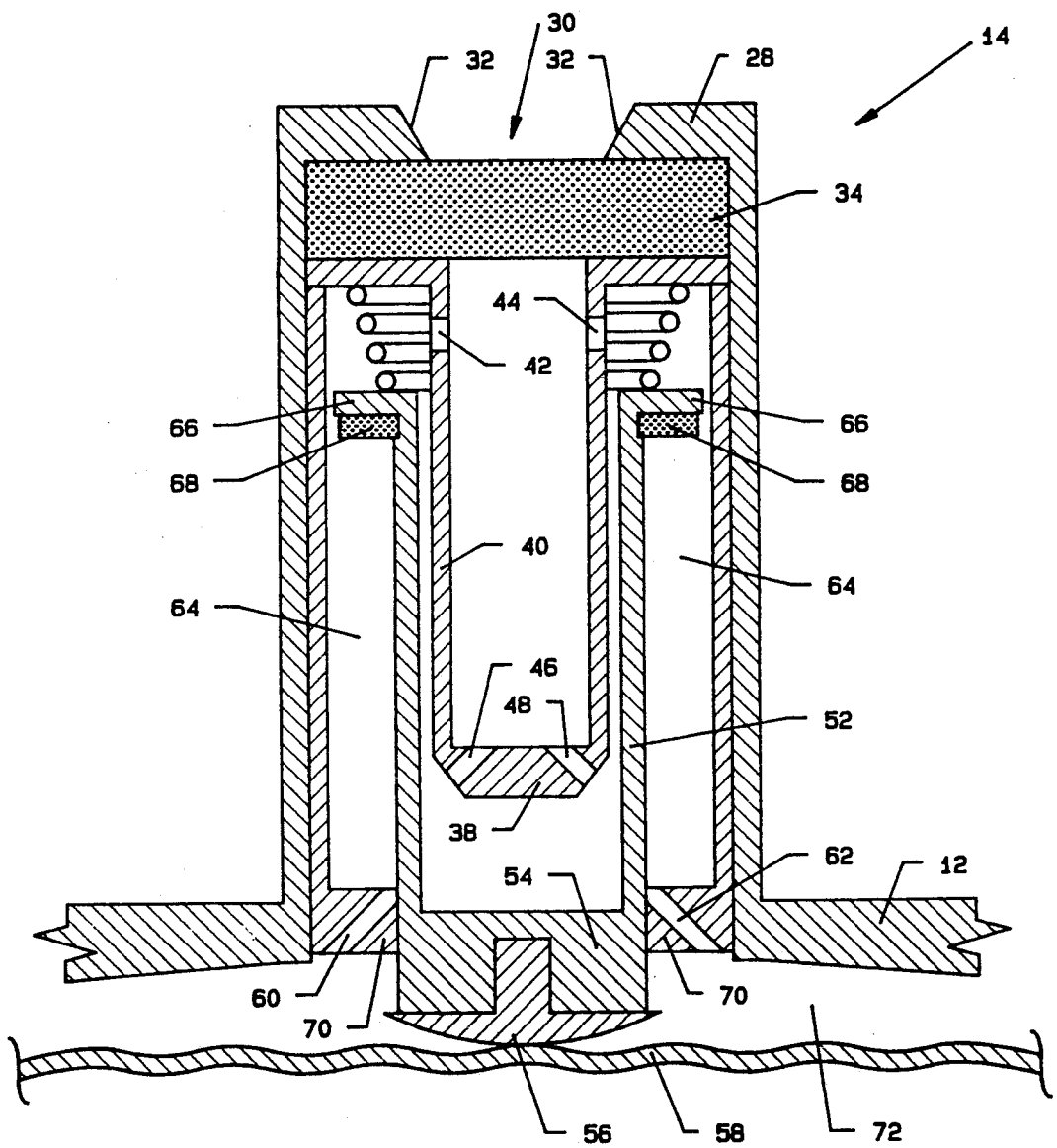
FIG. 4 is a detailed sectioned view of the major components of the automatic valve system.

FIG. 4 is a close up sectioned view of the major components of the automatic valve of the present invention. The inner surface of central lumen 30 of fill port 14 contains chamfer 32 to better guide needle 22 through septum 34 (see also FIG. 2). Distal of septum 34, central lumen 30 is continued by fixed cylinder 40. Needle stop 38 is located at the distal end of fixed cylinder 40. Liquid drug 72 is injected inside fixed cylinder 40 during the filling process. Liquid drug 72 exits fixed cylinder 40 via ports 42, 44, 46, and 48.

After exiting from ports 42, 44, 46, and 48, liquid drug 72 flows through outer chamber 64 to the upper chamber of the reservoir. Outer chamber 64 is in fluid communication with the upper chamber of the reservoir via valve passages 60 and 62 through valve seat 70.

Valve actuator 52 is movable within outer chamber 64. The coiled spring tends to force valve actuator 52 in the downward direction by acting against annular tab 66 of valve actuator 52. Fixedly attached to the opposite surface of annular tab 66 is compressible valve seal 68. The distal end 54 of valve actuator 52 is coupled to cushioned bumper 56 which rests against diaphragm 58. The tip can also be metal, the same as the rest of the actuator. Alternatively, it can be connected to the diaphragm and pulled up and down. Note that the coiled spring operating against annular tab 66 maintains cushioned bumper 56 in direct contact with diaphragm 58 as it moves to maintain the relative volumes within the upper and lower chambers (see also FIG. 3).

As the upper chamber of the reservoir is filled by the injection of liquid drug 72, diaphragm 58 is depressed, and valve actuator 52 is moved downward (i.e. distally) through the action of the coiled spring. The length of valve actuator 52 from annular tab 66 to distal end 54 is chosen such that compressible valve seal 68 sealingly engages valve seat 70 at the distal most excursion of diaphragm 58. This seals valve passages 60 and 62, thus preventing the injection of any further liquid drug 72 into the upper chamber of the reservoir.

DESCRIPTION OF THE ALTERNATIVE EMBODIMENT

Figure 5:
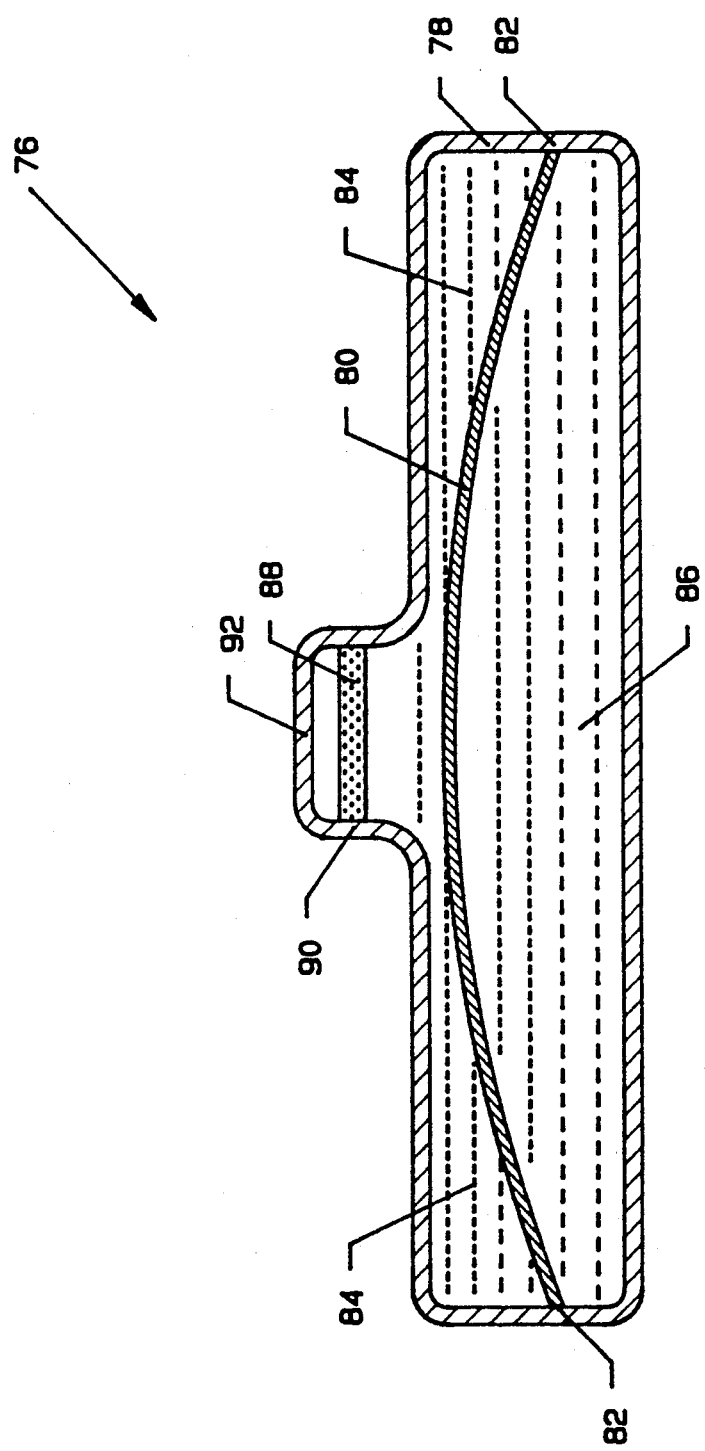
FIG. 5 is a cutaway partial view of an alternative embodiment of a drug administration device when nearly empty.

FIG. 5 is a partial side view of drug administration device 76 having an alternative embodiment diaphragm 80. Drug administration device 76 has an outside housing 78 similar to the embodiment previously discussed. Filling port 90 is raised to present aperture 92 for needle insertion as described above. Septum 88 is resealable and functions as described in accordance with the previously discussed embodiment.

Drug administration device 76 employs diaphragm 80 joined to housing 78 about ring 82 to separate the interior of housing 78 into medicament chamber 84 and backfill chamber 86. Diaphragm 80 is termed "snap dome" in the art as it is molded of a non-porous polymer into a dome shape. This makes diaphragm 80 into a two-state structure. That means that it requires energy to compress it from a first stable state into an unstable intermediate state, and it releases energy from that unstable intermediate state into a second stable state.

Diaphragm 80 is shown in the first stable state wherein medicament chamber 84 has a minimum volume and backfill chamber 86 has a maximum volume. This corresponds to drug administration device 76 being in the empty condition.

Figure 6:
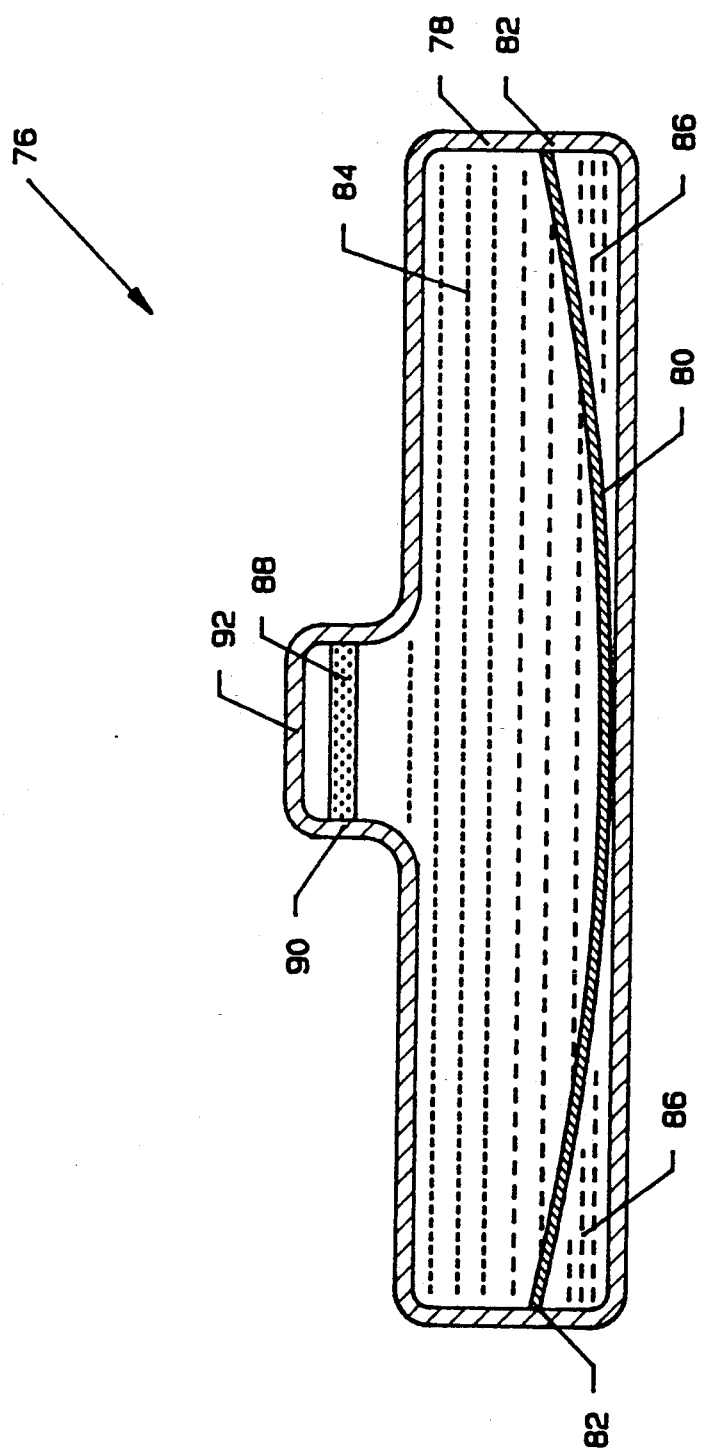
FIG. 6 is a view of the device of FIG. 5 when full.

FIG. 6 is a view of drug administration device 76 in the full condition. When this occurs, the volume of medicament chamber 84 is at a maximum and the volume of backfill chamber 86 is at a minimum volume.

Figure 7:
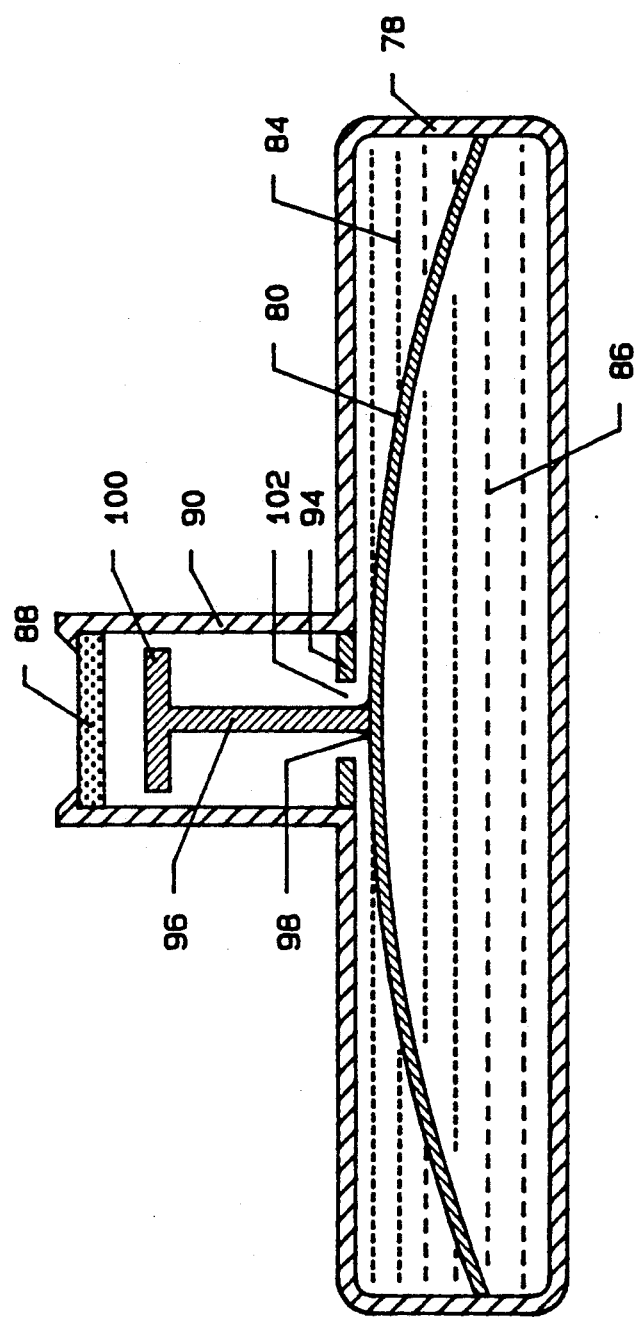
FIG. 7 is a view similar to FIG. 5 showing the operation of the automatic valve system; and, FIG. 8 is a view similar to FIG. 6 showing the operation of the automatic valve system.

FIG. 7 is a side sectioned view of drug administration device 76 showing operation of an alternative embodiment of an automatic safety valve, comprising passageway 102 of valve seat 94, valve 100 attached to one end of valve stem 96, and weld 98 attaching the opposite end of valve stem 96 to the surface of diaphragm 80. It can be seen that liquid can be infused through septum 88 into medicament chamber 84 through passageway 102 with valve 100 displaced from valve seat 94. In this condition, drug administration device 76 can be filled.

Figure 8:
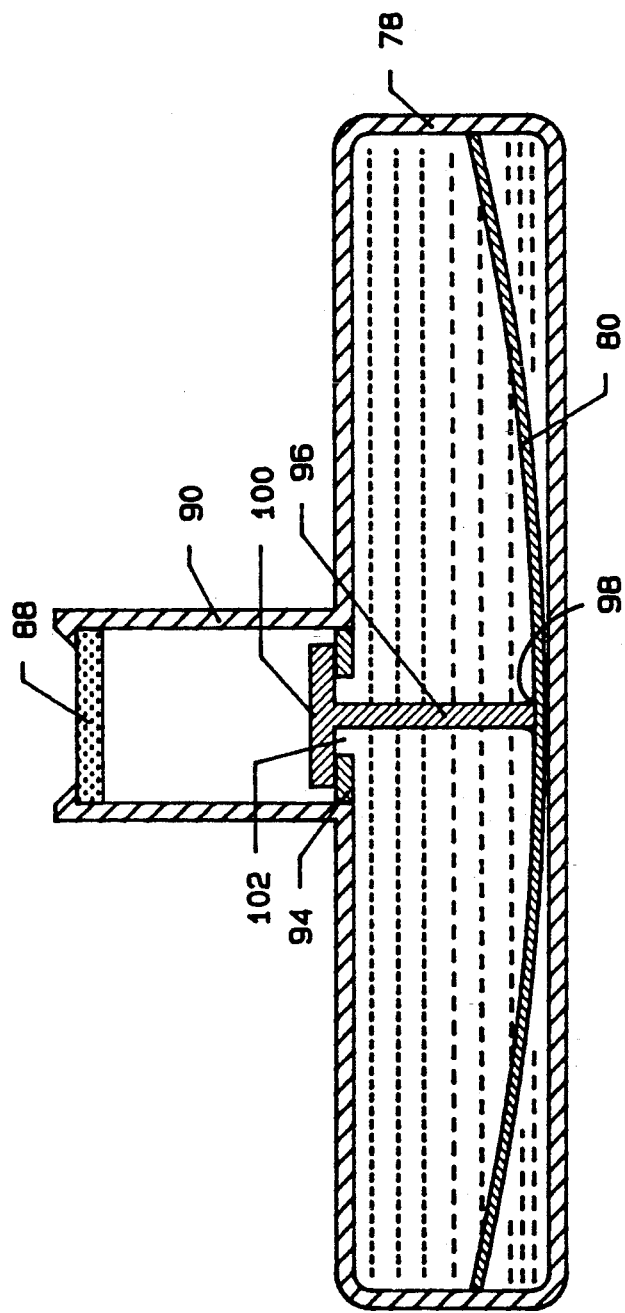

FIG. 8 is a side view of drug administration device 76 when filled. In this condition, diaphragm 80 goes to its second state. Valve stem 96, being fixedly attached to diaphragm 80, pulls valve 100 into sealing contact with valve seat 94. This closes passageway 102 and thus prevents overfilling.

Having thus described the preferred embodiments of the present invention, those of skill in the art will readily be able to adapt the teachings found herein to yet other embodiments within the scope of the claims hereto attached.

I claim:

1. An apparatus comprising:
   a. an implantable housing containing a reservoir;

b. a catheter in fluid communication with said reservoir;

c. a fill port in fluid communication with said reservoir; and, d. means coupled to said fill port for preventing said reservoir from becoming over filled from said fill port.

2. An apparatus according to claim 1 wherein said preventing means further comprises an automatic valve.

3. An apparatus according to claim 2 wherein said automatic valve closes upon said reservoir containing a predetermined volume.

4. An apparatus according to claim 3 wherein said reservoir further comprises two chambers separated by a diaphragm.

5. An apparatus according to claim 4 wherein a first chamber of said reservoir is filled with a means for compensating for volumetric changes.

6. An apparatus according to claim 5 wherein said compensating means is a fluid.

7. An apparatus according to claim 6 wherein said automatic valve further comprises a valve actuator in contact with said diaphragm.

8. An apparatus according to claim 7 wherein said valve actuator is held in contact with said diaphragm by a coiled spring.

9. An apparatus according to claim 8 wherein said valve actuator moves relative to said fill port.

10. An apparatus according to claim 9 wherein maximum distal movement of said valve actuator disturbs fluid coupling between said fill port and said reservoir.

* * * * *